United States Patent
Takahashi et al.

(10) Patent No.: US 12,022,844 B2
(45) Date of Patent: Jul. 2, 2024

(54) NUTRITIONAL COMPOSITION, FOOD/DRINK COMPOSITION USING NUTRITIONAL COMPOSITION, AND MODIFIED MILK POWDER USING NUTRITIONAL COMPOSITION

(71) Applicant: MORINAGA MILK INDUSTRY CO., LTD., Tokyo (JP)

(72) Inventors: Sachiko Takahashi, Kanagawa (JP); Noriyuki Iwabuchi, Kanagawa (JP)

(73) Assignee: MORINAGA MILK INDUSTRY CO., LTD., Tokyo (JP)

(*) Notice: Subject to any disclaimer, the term of this patent is extended or adjusted under 35 U.S.C. 154(b) by 872 days.

(21) Appl. No.: 16/975,778

(22) PCT Filed: Mar. 26, 2019

(86) PCT No.: PCT/JP2019/012894
§ 371 (c)(1),
(2) Date: Nov. 20, 2020

(87) PCT Pub. No.: WO2019/189200
PCT Pub. Date: Oct. 3, 2019

(65) Prior Publication Data
US 2021/0068414 A1 Mar. 11, 2021

(30) Foreign Application Priority Data
Mar. 29, 2018 (JP) ................................. 2018-065647

(51) Int. Cl.
| | | |
|---|---|---|
| A23L 29/30 | (2016.01) | |
| A23C 9/123 | (2006.01) | |
| A23C 9/13 | (2006.01) | |
| A23L 33/00 | (2016.01) | |
| A23L 33/125 | (2016.01) | |
| A23L 33/135 | (2016.01) | |

(52) U.S. Cl.
CPC .......... *A23C 9/1232* (2013.01); *A23C 9/1307* (2013.01); *A23L 29/30* (2016.08); *A23L 33/125* (2016.08); *A23L 33/135* (2016.08); *A23L 33/40* (2016.08)

(58) Field of Classification Search
CPC ..... A23C 9/1232; A23C 9/1307; A23L 29/30; A23L 33/125; A23L 33/135; A23L 33/40
USPC ........................................................ 426/43
See application file for complete search history.

(56) References Cited

U.S. PATENT DOCUMENTS

| 9,567,361 B2 | 2/2017 | Newburg et al. |
| 2009/0162323 A1 | 6/2009 | Boehm et al. |
| 2015/0010670 A1 | 1/2015 | Mills et al. |
| 2015/0119360 A1 | 4/2015 | Yamamoto et al. |
| 2017/0202864 A1* | 7/2017 | Gallardo ................ A23L 33/00 |
| 2017/0354696 A1 | 12/2017 | Albrecht et al. |

FOREIGN PATENT DOCUMENTS

| KR | 10-1589467 B1 | 1/2016 |
| WO | WO2012/158517 A1 | 11/2012 |
| WO | WO2013/161820 A1 | 10/2013 |
| WO | WO2014/086373 A1 | 6/2014 |
| WO | WO2019/106618 A1 | 6/2019 |

OTHER PUBLICATIONS

Ward, R. E. et al. Mol. Nut. Food Res. 51: 1398-1405 (Year: 2007).*
Extended European Search Report for European Patent App. No. 19775704.0 (Dec. 10, 2021).
Office Action issued by the Japanese Patent Office for Japanese Patent Application No. 2020-510924 (Dec. 20, 2022), and English translation.
Asakuma, S., et al., "Physiology of Consumption of Human Milk Oligosaccharides by Infant Gut-associated Bifidobacteria," J. Biol. Chem. 2011;286(40):34583-34592.
Turroni, F., et al., "Glycan Utilization and Cross-Feeding Activities by Bifidobacteria," Trends in Microbiol. 2018;26(4):339-350.
Egan, M., et al., "Metabolism of Sialic Acid by Bifidobacterium breve UCC2003," Appl. Environ. Microbiol. 2014;80:4414-4426.
Egan, M., et al., "Cross-feeding by Bifidobacterium breve UCC2003 during co-cultivation with Bifidobacterium bifidum PRL2010 in a mucin-based medium," BMC Microbiol. 2014;14:282, pp. 1-14.
Gotoh, A., et al., "Sharing of human milk oligosaccharides degradants within bifidobacterial communities in faecal cultures supplemented with Bifidobacterium bifidum," Sci. Rep. 2018, vol. 8:13958, pp. 1-14.
International Search Report for PCT Patent App. No. PCT/JP2019/012894 (Jun. 18, 2019).
Kitaoka, M., "Molecular mechanism on bifidus factor in human milk," Japanese Journal of Lactic Acid Bacteria, 2011, vol. 22, No. 1, pp. 15-24. (English abstract provided on p. 25).
Urashima, T., et al., "Biological significance of human milk oligosaccharides," Milk Sci. 2008;56(4):155-176.
Kitaoka, M., "Molecular mechanism how human milk oligosaccharides stimulate intestinal growth of bifidobacteria," Milk Sci. 2012;61(2):115-124.
Asakuma, S., et al., "Physiology of Consumption of Human Milk Oligsaccharides by Infant Gut-associated Bifidobacteria," J. Biol. Chem. 2011;286(40):34583-34592.

(Continued)

*Primary Examiner* — Hamid R Badr
(74) *Attorney, Agent, or Firm* — Cermak & McGowan LLP; Shelly Guest Cermak

(57) ABSTRACT

Provided is a method that makes it possible to promote proliferation of probiotics having a low ability to assimilate human milk oligosaccharides (HMOs), in the presence of HMOs. A nutritional composition is described that includes bacteria belonging to *Bifidobacterium bifidum*, one or more types of probiotics having a low ability to assimilate human milk oligosaccharides, and human milk oligosaccharides. The nutritional composition as described herein may be suitably used for foods/drinks, medicines, quasi-drugs, feeds, and the like.

9 Claims, No Drawings
Specification includes a Sequence Listing.

(56) References Cited

OTHER PUBLICATIONS

Examination Report No. 2 from Australian Patent App. No. 2019243093 (May 19, 2022).
Office Action from Chinese Patent App. No. 201980021823.3 (Sep. 29, 2022) with English language translation thereof.
Office Action issued by the China National Intellectual Property Administration for Chinese Application No. 201980021823.3 (Feb. 15, 2023) and English translation.
Office Action from Republic of Indonesia for Patent Application No. P00202006782 (Jan. 16, 2023) with English language translation thereof.
English Translation of Office Action from Republic of Indonesia (Jan. 16, 2023) for Patent Application No. P00202006782.

* cited by examiner

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial sequence
<220> FEATURE:
<223> OTHER INFORMATION: Forward primer of Bifidobacterium bifidum

<400> SEQUENCE: 1
ccacatgatc gcatgtgatt g                                              21

<210> SEQ ID NO 2
<211> LENGTH: 19
<212> TYPE: DNA
<213> ORGANISM: Artificial sequence
<220> FEATURE:
<223> OTHER INFORMATION: Reverse primer of Bifidobacterium bifidum

<400> SEQUENCE: 2
ccgaaggctt gctcccaaa                                                 19

<210> SEQ ID NO 3
<211> LENGTH: 20
<212> TYPE: DNA
<213> ORGANISM: Artificial sequence
<220> FEATURE:
<223> OTHER INFORMATION: Forward primer of Bifidobacterium longum subsp
      longum

<400> SEQUENCE: 3
ttccagttga tcgcatggtc                                                20

<210> SEQ ID NO 4
<211> LENGTH: 20
<212> TYPE: DNA
<213> ORGANISM: Artificial sequence
<220> FEATURE:
<223> OTHER INFORMATION: Reverse primer of Bifidobacterium longum subsp
      longum

<400> SEQUENCE: 4
gggaagccgt atctctacga                                                20

<210> SEQ ID NO 5
<211> LENGTH: 19
<212> TYPE: DNA
<213> ORGANISM: Artificial sequence
<220> FEATURE:
<223> OTHER INFORMATION: Forward primer of Bifidobacterium adlescentis

<400> SEQUENCE: 5
ctccagttgg atgcatgtc                                                 19

<210> SEQ ID NO 6
<211> LENGTH: 18
<212> TYPE: DNA
```

```
<213> ORGANISM: Artificial sequence
<220> FEATURE:
<223> OTHER INFORMATION: Reverse primer of Bifidobacterium adlescentis

<400> SEQUENCE: 6
cgaaggcttg ctcccagt                                                 18

<210> SEQ ID NO 7
<211> LENGTH: 17
<212> TYPE: DNA
<213> ORGANISM: Artificial sequence
<220> FEATURE:
<223> OTHER INFORMATION: Forward primer of Bifidobacterium catenulatum
      group

<400> SEQUENCE: 7
cggatgctcc gactcct                                                  17

<210> SEQ ID NO 8
<211> LENGTH: 18
<212> TYPE: DNA
<213> ORGANISM: Artificial sequence
<220> FEATURE:
<223> OTHER INFORMATION: Reverse primer of Bifidobacterium catenulatum
      group

<400> SEQUENCE: 8
cgaaggcttg ctcccgat                                                 18

<210> SEQ ID NO 9
<211> LENGTH: 18
<212> TYPE: DNA
<213> ORGANISM: Artificial sequence
<220> FEATURE:
<223> OTHER INFORMATION: Forward primer of Bifidobacterium pseudolongum

<400> SEQUENCE: 9
cacatgagcg catgcgag                                                 18

<210> SEQ ID NO 10
<211> LENGTH: 19
<212> TYPE: DNA
<213> ORGANISM: Artificial sequence
<220> FEATURE:
<223> OTHER INFORMATION: Reverse primer of Bifidobacterium pseudolongum

<400> SEQUENCE: 10
tccactcaac acggccgaa                                                19

<210> SEQ ID NO 11
<211> LENGTH: 18
<212> TYPE: DNA
<213> ORGANISM: Artificial sequence
<220> FEATURE:
<223> OTHER INFORMATION: Forward primer of Bifidobacterium animalis
      subsp lactis

<400> SEQUENCE: 11
gtggagacac ggtttccc                                                 18

<210> SEQ ID NO 12
<211> LENGTH: 20
<212> TYPE: DNA
<213> ORGANISM: Artificial sequence
<220> FEATURE:
<223> OTHER INFORMATION: Reverse primer of Bifidobacterium animalis
      subsp lactis
```

```
<400> SEQUENCE: 12
cacaccacac aatccaatac                                              20

<210> SEQ ID NO 13
<211> LENGTH: 19
<212> TYPE: DNA
<213> ORGANISM: Artificial sequence
<220> FEATURE:
<223> OTHER INFORMATION: Forward primer of Lactobacillus casei

<400> SEQUENCE: 13
cgagttctcg ttgatgatc                                               19

<210> SEQ ID NO 14
<211> LENGTH: 19
<212> TYPE: DNA
<213> ORGANISM: Artificial sequence
<220> FEATURE:
<223> OTHER INFORMATION: Reverse primer of Lactobacillus casei

<400> SEQUENCE: 14
aagattccct actgctgcc                                               19

<210> SEQ ID NO 15
<211> LENGTH: 19
<212> TYPE: DNA
<213> ORGANISM: Artificial sequence
<220> FEATURE:
<223> OTHER INFORMATION: Forward primer of Lactobacillus plantarum

<400> SEQUENCE: 15
agatttgatc atggctcag                                               19

<210> SEQ ID NO 16
<211> LENGTH: 20
<212> TYPE: DNA
<213> ORGANISM: Artificial sequence
<220> FEATURE:
<223> OTHER INFORMATION: Reverse primer of Lactobacillus plantarum

<400> SEQUENCE: 16
cggtattagc atctgtttcc                                              20

<210> SEQ ID NO 17
<211> LENGTH: 17
<212> TYPE: DNA
<213> ORGANISM: Artificial sequence
<220> FEATURE:
<223> OTHER INFORMATION: Forward primer of Lactobacillus acidophilus

<400> SEQUENCE: 17
acagattcac ttcggtg                                                 17

<210> SEQ ID NO 18
<211> LENGTH: 23
<212> TYPE: DNA
<213> ORGANISM: Artificial sequence
<220> FEATURE:
<223> OTHER INFORMATION: Reverse primer of Lactobacillus acidophilus

<400> SEQUENCE: 18
aaaggccagt tactacctct atc                                          23

<210> SEQ ID NO 19
```

```
<211> LENGTH: 24
<212> TYPE: DNA
<213> ORGANISM: Artificial sequence
<220> FEATURE:
<223> OTHER INFORMATION: Forward primer of Lactobacillus rhamnosus

<400> SEQUENCE: 19
gcaagtcgaa cgagttctga ttat                                         24

<210> SEQ ID NO 20
<211> LENGTH: 26
<212> TYPE: DNA
<213> ORGANISM: Artificial sequence
<220> FEATURE:
<223> OTHER INFORMATION: Reverse primer of Lactobacillus rhamnosus

<400> SEQUENCE: 20
gccgacaaca gttactctgc cgacca                                       26

<210> SEQ ID NO 21
<211> LENGTH: 23
<212> TYPE: DNA
<213> ORGANISM: Artificial sequence
<220> FEATURE:
<223> OTHER INFORMATION: Forward primer of Lactobacillus gasseri

<400> SEQUENCE: 21
gatgaatttg gtgcttgcac cag                                          23

<210> SEQ ID NO 22
<211> LENGTH: 19
<212> TYPE: DNA
<213> ORGANISM: Artificial sequence
<220> FEATURE:
<223> OTHER INFORMATION: Reverse primer of Lactobacillus gasseri

<400> SEQUENCE: 22
aagattccct actgctgcc                                               19
```

NUTRITIONAL COMPOSITION, FOOD/DRINK COMPOSITION USING NUTRITIONAL COMPOSITION, AND MODIFIED MILK POWDER USING NUTRITIONAL COMPOSITION

This application is a national phase entry under 35 U.S.C. § 371 of PCT Patent Application No. PCT/JP2019/012894, filed on Mar. 26, 2019, which claims priority under 35 U.S.C. § 119 to Japanese Patent Application No. 2018-065647, filed Mar. 29, 2018, both of which are incorporated by reference.

TECHNICAL FIELD

The present technology relates to a nutritional composition capable of promoting proliferation of probiotics having a low ability to assimilate human milk oligosaccharides (hereinafter, also referred to as "HMOs").

BACKGROUND ART

Bifidobacteria are indigenous bacteria within an intestinal tract of mammals including humans, and are known to have an action of inhibiting proliferation of pathogenic intestinal bacteria within the intestinal tract.

In general, Bifidobacteria are dominant in intestinal flora (intestinal bacteria flora) of a healthy babies, but gradually decrease with age, and then putrefactive bacteria such as *Escherichia coli* or bacteria of the genus *Clostridium* increase, thereby adversely affecting the health of a host (a human). Thus, in order to maintain a healthy state for a long time, it is important to maintain intestinal flora where the Bifidobacteria are dominant.

HMOs are contained in breast milk at 10 to 20 g/L, and are a mixture of 130 or more types of oligosaccharides. Their structures include 13 different types of core structures to which fucose and sialic acid are added. The ratio of fucosylated neutral sugar is high in human milk, and representatively, include 2'-fucosyl lactose (hereinafter, also referred to as "2'-FL"), lacto-N-fucopentaose I (hereinafter, also referred to as "LNFPI"), lacto-N-difucohexaose I (hereinafter, also referred to as "LNDFP I"), and lacto-N-tetraose (hereinafter, also referred to as "LNT"). These four types account for ⅓ to ¼ of all human milk oligosaccharides. Oligosaccharides containing lacto-N-biose are set as type I, and oligosaccharides containing N-acetyllactosamine (Gal (β1-4)GlcNAc) are set as type II. In human milk, the amount of LNT or LNFP1 of type I is higher than that of lacto-N-neotetraose (hereinafter, also referred to as "LNnT") or lacto-N-fucopentaose III of type II. The coexistence of type I and type II, and the preference of type I are distinctive characteristics of human milk oligosaccharides, which are different from other types of milk oligosaccharides (see Non-Patent Literatures 1 and 2).

HMOs present in breast milk, 2'-FL and LNnT, have a Bifidobacteria proliferation activity, are known to act as a growth factor of Bifidobacteria by being selectively used by Bifidobacteria, and are important in the formation of Bifidobacteria-dominant intestinal flora. Also, HMOs may be synthesized, and therefore have industrial applicability (see Patent Literature 1).

Bifidobacteria metabolize some HMOs by using a GNB/LNB pathway specific to the Bifidobacteria. This pathway is present in many species often found in babies, but not present in Bifidobacteria often found in the intestinal tract of adults. Among the four bacterial species of *Bifidobacterium longum* subspecies *longum*, *Bifidobacterium longum* subspecies *infantis*, *Bifidobacterium breve*, and *Bifidobacterium bifidum*, which are the Bifidobacteria often found in babies, the two bacterial species of *Bifidobacterium longum* subspecies *infantis* and *Bifidobacterium bifidum* have been reported as bacterial species that may use HMOs as a sole carbon source (see Non-Patent Literature 3).

CITATION LIST

Patent Literature

Patent Literature 1: WO2014/086373

Non-Patent Literature

Non-Patent Literature 1: Japanese Journal of Lactic Acid Bacteria Vol. 22, No. 1 2011
Non-Patent Literature 2: Milk Science Vol. 56, No. 4 2008
Non-Patent Literature 3: Milk Science Vol. 61, No. 2. 2012
Non-Patent Literature 4: THE JOURNAL OF BIOLOGICAL CHEMISTRY VOL. 286, NO. 40

SUMMARY OF INVENTION

Technical Problem

In metabolizing HMOs, as described above, among Bifidobacteria, there are bacteria having no or low ability to assimilate HMOs, while there are also bacteria that are able to assimilate HMOs, such as *Bifidobacterium longum* subspecies *infantis* and *Bifidobacterium bifidum*. Then, in metabolizing HMOs, for example, *Bifidobacterium longum* subspecies *infantis* incorporates HMOs into the microbial cells, in use, while *Bifidobacterium bifidum* temporarily promotes accumulation of lactose outside microbial cells by decomposing these oligosaccharides with an extracellular enzyme (see Non-Patent Literatures 3 and 4).

As described above, among bacteria, there are bacteria having no or low ability to assimilate HMOs. However, even among such bacteria, there are many bacteria that may be used as good bacteria. Therefore, even probiotics having no or low ability to assimilate human milk oligosaccharides (hereinafter, also referred to as "HMOs") are useful as a nutritional composition as long as proliferation is possible in the presence of HMOs.

Therefore, a main object of the present technology is to provide a technique that makes it possible to promote proliferation of probiotics having a low ability to assimilate human milk oligosaccharides (HMOs), in the presence of HMOs.

Solution to Problem

In order to solve the above problems, the present inventors, etc. observed the fact that *Bifidobacterium bifidum* temporarily promote accumulation of lactose outside microbial cells by decomposing HMOs with an extracellular enzyme, and then found that proliferation of probiotics having a low ability to assimilate HMOs is promoted when probiotics having a low ability to assimilate HMOs, *Bifidobacterium bifidum*, and HMOs are co-cultured.

That is, the present technology provides a nutritional composition containing bacteria belonging to *Bifidobacterium bifidum*, one or more types of probiotics having a low ability to assimilate human milk oligosaccharides, and human milk oligosaccharides.

In the nutritional composition according to the present technology, as for the human milk oligosaccharides, 2'-fucosyllactose and/or lacto-N-neotetraose may be used.

In the nutritional composition according to the present technology, as for the probiotics, bacteria of the genus *Bifidobacterium*, excluding the bacteria belonging to *Bifidobacterium bifidum*, and/or *lactobacilli* may be used.

In this case, as for the bacteria of the genus *Bifidobacterium*, excluding the bacteria belonging to *Bifidobacterium bifidum*, at least one bacterium selected from *Bifidobacterium longum* subspecies *longum, Bifidobacterium adolescentis, Bifidobacterium pseudocatenulatum, Bifidobacterium animalis* subspecies *lactis, Bifidobacterium breve*, and *Bifidobacterium pseudolongum* may be used.

Also, as for the *lactobacilli*, at least one bacterium selected from *Lactobacillus paracasei, Lactobacillus plantarum, Lactobacillus acidophilus, Lactobacillus rhamnosus*, and *Lactobacillus gasseri* may be used.

In the nutritional composition according to the present technology, as for the bacteria belonging to *Bifidobacterium bifidum*, at least one bacterium selected from *Bifidobacterium bifidum* ATCC29521, *Bifidobacterium bifidum* (NITE BP-02429), *Bifidobacterium bifidum* (NITE BP-1252), *Bifidobacterium bifidum* (NITE BP-02431), *Bifidobacterium bifidum* (NITE BP-02648), *Bifidobacterium bifidum* (NITE BP-02432), and *Bifidobacterium bifidum* (NITE BP-02433) may be used.

The nutritional composition according to the present technology may be used for a food/drink composition or modified milk powder.

Advantageous Effects of Invention

According to the present technology, it is possible to promote proliferation of probiotics having a low ability to assimilate human milk oligosaccharides (HMOs), in the presence of HMOs. The effects described herein are not necessarily limited, and may be any of the effects described in the present technology.

DESCRIPTION OF EMBODIMENTS

Hereinafter, a suitable embodiment for carrying out the present technology will be described. The embodiment to be described below is described as an example of a representative embodiment of this disclosure, by which the scope of the present technology is not to be narrowly construed. In this specification, regarding the numerical range expressed as "lower limit to upper limit," the upper limit may be "or less" or "less than," and the lower limit may be "or more" or "greater than." Also, in this specification, the percentage is expressed by mass unless otherwise specified.

1. Nutritional Composition

A nutritional composition according to the present technology contains at least the following components: (1) bacteria belonging to *Bifidobacterium bifidum*, (2) one or more types of probiotics having a low ability to assimilate human milk oligosaccharides, and (3) human milk oligosaccharides. Hereinafter, each of these components will be described in detail.

(1) Bacteria Belonging to *Bifidobacterium bifidum*

As for bacteria belonging to *Bifidobacterium bifidum* which may be used in the present technology, one type or two or more types of known or unknown bacteria belonging to *Bifidobacterium bifidum* may be freely selected and used as long as the effect of the present technology is not impaired. Specifically, for example, examples may include *Bifidobacterium bifidum* ATCC29521, *Bifidobacterium bifidum* (NITE BP-02429), *Bifidobacterium bifidum* (NITE BP-1252), *Bifidobacterium bifidum* (NITE BP-02431), *Bifidobacterium bifidum* (NITE BP-02648), *Bifidobacterium bifidum* (NITE BP-02432), *Bifidobacterium bifidum* (NITE BP-02433), *Bifidobacterium bifidum* (FERM BP-791), *Bifidobacterium bifidum* (FERM P-11788), *Bifidobacterium bifidum* (FERM P-11791), *Bifidobacterium bifidum* (NITE BP-31), *Bifidobacterium bifidum* G9-1, *Bifidobacterium bifidum* BF-1, *Bifidobacterium bifidum* Rosen-71, *Bifidobacterium bifidum* (NCDO 1453), and the like.

*Bifidobacterium bifidum* ATCC29521 may be obtained from the American Type Culture Collection (address: 12301 Parklawn Drive, Rockville, Maryland 20852, United States of America).

*Bifidobacterium bifidum* (NITE BP-02429), *Bifidobacterium bifidum* (NITE BP-02431), *Bifidobacterium bifidum* (NITE BP-02432), and *Bifidobacterium bifidum* (NITE BP-02433) were internationally deposited with deposit numbers of NITE BP-02429, NITE BP-02431, NITE BP-02432, and NITE BP-02433 under the Budapest Treaty at Patent Microorganism Depository Center, National Institute of Technology and Evaluation (NITE) (Room No. 122, 2-5-8 Kazusakamatari Kisarazu Chiba 292-0818), on Feb. 21, 2017.

*Bifidobacterium bifidum* (NITE BP-1252) was internationally deposited with a deposit number of NITE BP-1252 under the Budapest Treaty at Patent Microorganism Depository Center, National Institute of Technology and Evaluation (NITE) (Room No. 122, 2-5-8 Kazusakamatari Kisarazu Chiba 292-0818), on Feb. 23, 2012.

*Bifidobacterium bifidum* (NITE BP-02648) was deposited with a deposit number of NITE BP-02648 at Patent Microorganism Depository Center, National Institute of Technology and Evaluation (NITE) (Room No. 122, 2-5-8 Kazusakamatari Kisarazu Chiba 292-0818), on Feb. 26, 2018.

The strain specified by the above-exemplified strain name is not limited to the strain itself that has been deposited or registered in a predetermined institution with the corresponding strain name (hereinafter, for convenience of explanation, also referred to as a "deposited strain"), but also includes a strain substantially equivalent thereto (also referred to as a "derivative strain" or an "induced strain"). That is, for example, "*Bifidobacterium bifidum* ATCC29521" is not limited to the strain itself that has been deposited in the depository with a deposit number of *Bifidobacterium bifidum* ATCC29521, but also includes a strain substantially equivalent thereto.

The strain substantially equivalent to the deposited strain may be, for example, a derivative strain whose parent strain is the corresponding deposited strain. The derivative strain may include a strain bred from the deposited strain or a strain naturally occurring from the deposited strain.

As substantially identical strains and derivative strains, the following strains may be mentioned:

(1) a strain determined as an identical strain by an RAPD (Randomly Amplified Polymorphic DNA) method or a PFGE (Pulsed-field gel electrophoresis) method (described in Probiotics in food/Health and nutritional properties and guidelines for evaluation 85, Page 43)

(2) a strain that has only the genes derived from the corresponding deposited strain, has no foreign-derived genes, and has a DNA identity of 95% or more (3) a strain bred from the corresponding strain (a strain having the same traits, including genetic engineering alterations, mutations, and natural mutations)

In metabolizing HMOs, such bacteria belonging to *Bifidobacterium bifidum* temporarily promote accumulation of lactose outside of the microbial cells by decomposing HMOs with an extracellular enzyme. The accumulated lactose may be used by probiotics having a low ability to assimilate human milk oligosaccharides, which will be described below, so that the probiotics having a low ability to assimilate human milk oligosaccharides may proliferate.

(2) Probiotics Having Low Ability to Assimilate Human Milk Oligosaccharides

As for probiotics having a low ability to assimilate human milk oligosaccharides, which may be used in the present technology, one type or two or more types of microbial cells may be freely selected from known or unknown probiotics having a low ability to assimilate human milk oligosaccharides, as long as the effect of the present technology is not impaired.

In the present invention, "the ability to assimilate human milk oligosaccharides is low" means that bacteria are not only less able to utilize sugars, but also less able to metabolize and proliferate when cultured in a medium containing human milk oligosaccharides as a carbon source, as compared to when cultured in a medium containing sugars such as glucose or lactose, which are generally assimilated by Bifidobacteria and *lactobacilli* (as probiotics), as a carbon source.

For example, the ability to assimilate human milk oligosaccharides may be determined by measuring the uptake rate of human milk oligosaccharides introduced into cells, as an index, and may be calculated by measuring whether human milk oligosaccharides are decreasing with time after the start of culturing. Otherwise, confirmation may be performed by checking the turbidity or the specific growth rate of microorganisms in a medium containing only human milk oligosaccharides, as a carbon source.

The specific growth rate of a microorganisms is defined as an increase of cells per unit time. The case of "the ability to assimilate human milk oligosaccharides is low" means that the specific growth rate is reduced to 80% or less, preferably 70% or less, more preferably 50% or less, further preferably 10% or less in a case of human milk oligosaccharides as a carbon source as compared to that in a medium having glucose or lactose as a carbon source. Specifically, for example, in the present technology, as for probiotics having a low ability to assimilate human milk oligosaccharides, bof the genus *Bifidobacterium*, excluding bacteria belonging to *Bifidobacterium bifidum*, and/or *lactobacilli* may be mentioned.

In the present invention, probiotic microbial cells having no assimilability of human milk oligosaccharides may be used. The probiotic microbial cells having no assimilability of human milk oligosaccharides mean microbial cells which cannot use human milk oligosaccharides at all, or which are partially deficient in a metabolic pathway, and do not have a transporter that introduces metabolized sugar into the body.

More specifically, as for bacteria of the genus *Bifidobacterium*, excluding bacteria belonging to *Bifidobacterium bifidum*, *Bifidobacterium longum* subspecies *longum*, *Bifidobacterium adolescentis*, *Bifidobacterium pseudocatenulatum*, *Bifidobacterium animalis* subspecies *lactis*, *Bifidobacterium breve*, *Bifidobacterium pseudolongum*, and the like may be mentioned.

Further specifically, *Bifidobacterium longum* subspecies *longum* ATCC15707, *Bifidobacterium longum* subspecies *longum* BB536, *Bifidobacterium adolescentis* ATCC15703, *Bifidobacterium pseudocatenulatum* ATCC27919, *Bifidobacterium animalis* subspecies *lactis* DSM10140, *Bifidobacterium animalis* subspecies *lactis* MCC-525, *Bifidobacterium breve* ATCC15700, *Bifidobacterium pseudolongum* ATCC25526, *Bifidobacterium longum* (FERM P-10657), *Bifidobacterium animalis* subspecies *lactis* Bb-12 DSM1595, *Bifidobacterium animalis* subspecies *lactis* GCL2505, *Bifidobacterium animalis* subspecies *lactis* CNCMI-2494, *Bifidobacterium animalis* subspecies *lactis* LAFTI B94, *Bifidobacterium animalis* subspecies *lactis*, *Bifidobacterium longum* Rosen-175, *Bifidobacterium animalis* subspecies *animalis*, *Bifidobacterium animalis* subspecies *lactis* HNO19, and the like may be mentioned.

Also, as for *lactobacilli*, *Lactobacillus paracasei*, *Lactobacillus plantarum*, *Lactobacillus acidophilus*, *Lactobacillus rhamnosus*, *Lactobacillus gasseri*, and the like may be mentioned.

More specifically, *Lactobacillus paracasei* ATCC25302, *Lactobacillus plantarum* ATCC14917, *Lactobacillus acidophilus* ATCC4356, *Lactobacillus rhamnosus* ATCC7469, *Lactobacillus gasseri* ATCC33323, *Lactobacillus gasseri* FERM BP-10953, *Lactobacillus gasseri* FERN BP-6999, *Lactobacillus gasseri* (NITE BP-224R), *Lactobacillus delbrueckii* subspecies *bulgaricus* (FERN P-17227), *Lactobacillus rhamnosus* ATCC53103, *Lactobacillus reuteri* DSM17938, *Bacillus coagulans* GBI-30, *Lactobacillus acidophilus*, *Lactobacillus acidophilus* LAFTI L10, *Lactobacillus casei* LAFTI (registered trademark) L26, *Lactobacillus casei* LAFTI (registered trademark) L26, *Lactococcus lactis* subspecies *lactis* Rosen-1058, *Lactobacillus paracasei* NCC2461, *Lactobacillus johnsonii* NCC533, *Lactobacillus rhamnosus* Rosell-11, *Lactobacillus acidophilus* Rosen-52, *Lactobacillus casei* Lactobacillus casei shirota strains, and the like may be mentioned.

These probiotics having a low ability to assimilate human milk oligosaccharides may proliferate by using lactose produced when HMOs are metabolized by the above described bacteria belonging to *Bifidobacterium bifidum*. More preferably, it is desirable that the specific growth rate of probiotics increases by culturing together with bacteria belonging to *Bifidobacterium bifidum*. For example, it means that the specific growth rate is increased to 105% or more, preferably 110% or more, more preferably 120% or more in a case of human milk oligosaccharides as a carbon source as compared to that in a medium having glucose or lactose as a carbon source.

In the present technology, "probiotics" mean live bacteria that exhibit a beneficial action on human health.

(3) Human Milk Oligosaccharides (HMOs)

HMOs are a generic term for oligosaccharides having three or more sugars, excluding lactose that is present in a small amount in breast milk. Mammalian milk has 12 series of core skeletons such as lacto-N-tetraose (LNT), lacto-N-neotetraose (LNnT), lacto-N-hexaose (LNH), and lacto-N-neohexaose (LNnH). Lewis a, b, x and α2-3/2-6N-Acetylneuraminic acid are added to these skeletons, so that there are as many as 100 possible variations of sugar chains.

As for HMOs that may be used in the present technology, one type or two or more types of known or unknown HMOs, which are oligosaccharides that may be used by bacteria belonging to *Bifidobacterium bifidum*, and also may not be used by the probiotics, may be freely selected and used as long as the effect of the present technology is not impaired. Specifically, for example, L-fucose, Lacto-N-fucopentaose I, Lacto-N-fucopentaose II, 2'-Fucosyllactose, 3'-Fucosyllactose, Lacto-N-fucopentaose III, 3'-Fucosyllacto-N-hexaose, Lacto-N-difucohexaose I, Lacto-difucotetraose, Lacto-difucohexaose I, Lactodifucohexaose II, Lacto-N-tetraose, Difucosyl syalyllacto-N-hexaose, Syalyllacto-N-tetraose, Fucosylsyalyl lacto-N-hexaose I, 3'-Fucosylsialyl lacto-N-tetraose(Fuc 1, 2 Gal, Fuc 1, 4 Gal NAC), Lacto-N-neotetraose, 3'-Sialyl-3-fucosyllactose, Disialomonofucosyllacto-N-neohexaose, Monofucosylmonosialyl lacto-N-octaose, Sialyllacto-N-fucohexaose II, Disialyllacto-N-fucopentaose II, Monofucosyldisialyllacto-N-tetraose, 2'-Sialyllactose, 2'-Sialyllactosamine, 3'-Sialyllactose, 3'-Sialyllactosamine, 6'-Sialyllactose, 6'-Sialyllactosamine, Sialyllacto-N-neotetraose c, Monosialyllacto-N-hexaose, Disialyllacto-N-hexaose I, Monosialyllacto-N-neohexaose I, Monosialyllacto-N-neohexaose II, Disialyllacto-N-neohexaose, Disialyllacto-N-tetraose, Disialyllacto-N-hexaose II, Sialyllacto-N-tetraose a, Disialyllacto-N-hexaose I, Sialyllacto-N-tetraose b, 2'-Fucosyllacto-N-hexaose, 3'-Fucosyllacto-N-neohexaose, 2'-Fucosyl-N-acetylglucosamine, Lacto-N-fucopentaose V, Lacto-N-hexaose, Para-lacto-N-hexaose, Lacto-N-neohexaose, Para-lacto-N-neohexaose, Monofucosyllacto-N-hexaose II, Isomeric fucosylated lacto-N-hexaose (1), Isomeric fucosylated lacto-N-hexaose (3), Isomeric fucosylated lacto-N-hexaose (2), Difucosyl-para-lacto-N-neohexaose, Difucosyl-para-lacto-N-hexaose, 2' 3'-Difucosyllacto-N-hexaose, Lacto-N-neoocataose, Para-lacto-N-octanose, Iso-lacto-N-octaose, Lacto-N-octaose, Monofucosyllacto-neoocataose, Monofucosyllacto-N-ocataose, Difucosyllacto-N-octaose I, Difucosyllacto-N-octaose II, Difucosyllacto-N-neoocataose II, Difucosyllacto-N-neoocataose I, Lacto-N-decaose, Trifucosyllacto-N-neoocataose, Trifucosyllacto-N-octaose, Trifucosyl-iso-lacto-N-octaose, Lacto-N-difuco-hexaose II, Sialyl-lacto-N-tetraose a, Sialyl-lacto-N-tetraose b, Sialyl-lacto-N-tetraose c, Sialyl-fucosyl-lacto-N-tetraose I, Sialyl-fucosyl-lacto-N-tetraose II, Disialyl-lacto-N-tetraose, Lacto-N-neotetraose, etc. and combinations thereof may be mentioned.

Among these, 2'-fucosyllactose (hereinafter, also referred to as "2'-FL"), lacto-N-fucopentaose I (hereinafter, also referred to as "LNFPI"), lacto-N-difucohexaose I (hereinafter, also referred to as "LNDFP I") and lacto-N-neotetraose (hereinafter, also referred to as "LNnT") may be used.

2. Application of Nutritional Composition According to the Present Technology

When the nutritional composition of the present invention is administered, promotion of proliferation of probiotics acting on good bacteria may be expected. That is, as the probiotics proliferate in the intestine, the intestinal flora is improved. The improvement of the intestinal flora makes it possible to improve or prevent, and treat diseases caused by the intestinal flora.

As for diseases caused by the intestinal flora, inflammatory colitis, ulcerative colitis, irritable colitis, a colorectal cancer, diabetes, arteriosclerosis, and the like may be mentioned.

Also, when the nutritional composition of the present invention is administered, immune function is enhanced. The enhancement of the immune function makes it possible to prevent or improve, and treat allergies such as pollen allergy, asthma, and atopic dermatitis.

The nutritional composition according to the present technology may be suitably used in foods/drinks, medicines, quasi-drugs, feeds, and the like.

The application of this embodiment may be for a therapeutic purpose use, or a non-therapeutic purpose use.

The "non-therapeutic purpose" is a concept that does not include a medical act, that is, an act of treating a human body by treatment. For example, health promotion, aesthetic treatment, and the like may be mentioned.

"Improvement" refers to improvement of a disease, a symptom or a condition; prevention or delay of deterioration of a disease, a symptom or a condition; or reversal, prevention or delay of progression of a disease or a symptom.

"Prevention" refers to prevention or delay of the onset of a disease or a symptom in the application target, or risk reduction of a disease or a symptom of the application target.

In each nutritional composition, it is desirable to administer probiotics at about $10^3$ to about $10^{12}$ CFU/g per dosage unit, but values higher than these are also acceptable. When the probiotic composition is administered to an adult (that is, a human over age 16), it is desirable to administer probiotics at a dose of, preferably, at least $10^6$ CFU/g, more preferably $10^8$ CFU/g. When the probiotic composition is administered to a child (that is, a human under age 16), it is desirable to administer probiotics in the range of preferably about $10^6$ to about $10^8$ CFU/g. CFU indicates a unit for colony formation: a colony forming unit.

It is desirable that the administration subject of the present invention is an infant.

Infants include babies and preschoolers, more particularly include babies, preschoolers, and newborn babies, and more particularly include babies, preschoolers, newborn babies, premature babies, preterm babies, and low birth weight infants. In the present invention, the species of the infants include a human unless otherwise specified. The baby refers to a child in infancy, and the infancy refers to a period during which milk such as breast milk is a main nutritional source. In the case of humans, the infancy usually corresponds to the age under 1. The preschooler usually refers to a child in a preschool period. The newborn baby refers to a child in a neonatal period, and the neonatal period means a period soon after the birth. In the case of humans, the neonatal period usually means within four weeks after the birth.

Also, in the present invention, in addition to human milk oligosaccharides, prebiotics may also be used together. Prebiotics are indigestible food ingredients which positively affect the host and improve the health of the host, by selectively changing the proliferation and activity of certain bacteria within the large intestine.

Prebiotics are not particularly limited as long as the effect of the present invention may be further obtained when they are ingested together with the present bacteria or a culture thereof, but, for example, lactulose, raffinose, galactooligosaccharides, fructooligosaccharides, soybean oligosaccharides, lacto-fructo oligosaccharides, xylo oligosaccharides, isomalto oligosaccharides, coffee bean manno-oligosaccharides, gluconic acid, polydextrose, inulin, etc. are preferred. Among these, lactulose, raffinose, galactooligosaccharides, and the like are more preferred, and lactulose, raffinose and galactooligosaccharides are further preferred.

<Food/Drink>

The nutritional composition according to the present technology may be added to a conventionally known food/drink in preparation, or may be mixed with a food/drink raw material so as to produce a new food/drink.

The food/drink using the nutritional composition according to the present technology may have any form such as liquids, pastes, solids, or powder, and not only tablet confectioneries, liquid foods, etc., but also, for example, flour products, instant foods, processed agricultural products, processed seafood products, processed livestock products, milk/dairy products, oils and fats, basic seasonings, complex seasonings/foods, frozen foods, confectioneries, drinks, commercially available products other than these, etc. may be mentioned.

Examples of the flour product may include bread, macaroni, spaghetti, noodles, cake mix, frying powder, bread crumbs, etc.

Examples of the instant food may include instant noodles, cup noodles, retort/cooked foods, cooked cans, microwave foods, instant soup/stew, instant miso soup/soup, canned soup, freeze dried foods, other instant foods, etc.

Examples of the processed agricultural product may include canned agricultural products, canned fruits, jams/marmalades, pickles, boiled beans, dried agricultural products, cereals (processed grain products), etc.

Examples of the processed seafood product may include canned seafoods, fish-flesh hams/sausages, seafood paste foods, seafood delicacies, tsukudani, etc.

Examples of the processed livestock product may include canned livestock/pastes, meat hams/sausages, etc.

Examples of the milk/dairy product may include fermented milk, processed milk, milk drinks, yogurts, lactic beverages, cheese, ice creams, modified milk powder, cream, other dairy products, etc.

Examples of the oil and fat may include butter, margarines, vegetable oils, etc.

As the basic seasoning, for example, soy sauces, miso, sauces, processed tomato seasonings, mirins, vinegars, etc. may be mentioned, and as the complex seasoning/food, cooking mix, curry sauces, spicy soy sauces, dressings, mentsuyu, spices, other complex seasonings, etc. may be mentioned.

Examples of the frozen food may include frozen food ingredients, semi-cooked frozen foods, cooked frozen foods, etc.

Examples of the confectionery may include caramels, candies, chewing gums, chocolates, cookies, biscuits, cakes, pies, snacks, crackers, Japanese sweets, rice confectioneries, bean confectioneries, dessert confectioneries, other confectioneries, etc.

Examples of the drink may include carbonated drinks, natural fruit juices, fruit juice drinks, fruit juice-containing soft drinks, pulp drinks, granule-containing fruit drinks, vegetable-based drinks, soymilk, soymilk drinks, coffee drinks, tea drinks, powdered drinks, concentrated drinks, sports drinks, nutritional drinks, alcohol drinks, other favorite drinks, etc.

Examples of the other commercially available foods may include weaning foods, furikake, ochazuke seaweed, etc.

The amount of bacteria belonging to *Bifidobacterium bifidum* in the food/drink according to the present technology may be freely set as long as the effect of the present technology is not impaired. In the present technology, in particular, the amount of bacteria belonging to *Bifidobacterium bifidum* in the food/drink may be set to $10^3$ to $10^{12}$ CFU/mL or g with respect to the final composition of the food/drink.

The content of probiotics having a low ability to assimilate human milk oligosaccharides in the food/drink according to the present technology may be freely set as long as the effect of the present technology is not decreased or inhibited. In the present technology, in particular, the amount of probiotics having a low ability to assimilate human milk oligosaccharides in the food/drink may be set to $10^3$ to $10^{12}$ CFU/mL or g with respect to a final composition of the food/drink.

The amount of HMOs in the food/drink according to the present technology may be freely set as long as the effect of the present technology is not decreased or inhibited. In the present technology, in particular, the amount of HMOs in the food/drink may be set to 0.3% to 5.0% with respect to a final composition of the food/drink.

Functionality Labeled Food/Drink

Also, the foods/drinks and the like defined in the present technology may also be provided or sold as foods/drinks labeled with a specific application (particularly, a health application) or a function.

The action of "labeling" includes all actions of informing consumers of the above application, and all expressions correspond to the action of "labeling" of the present technology regardless of the purpose of a label, the contents of a label, and a target object and a medium of labeling, as long as the above application may be recalled or realized.

Also, it is desirable that "labeling" is expressed so the consumers can directly recognize the above application. Specifically, an action of assignment and delivery of a product or a product packaging related to a food or a drink (on which the above application is described), and display and importation for the assignment or delivery; and an action of displaying or distributing advertisements, a price list, or a transaction document related to the product, on which the above application is described, or providing information having any of these as its content, on which the above application is described, by an electromagnetic (the Internet, etc.) method may be mentioned.

Meanwhile, as for the label contents, a label permitted by the government or the like (for example, a label or the like that is approved in accordance with various systems specified by the government, and is applied in the form based on such approval) is preferred. Also, it is desirable that such label contents are attached to packaging, containers, catalogs, pamphlets, advertising materials at a sales site such as a POP, other documents and the like.

Also, as for the "label," labels for health foods, functional foods, foods for patients, enteral nutritional foods, special purpose foods, health functional foods, foods for specified health uses, functionality labeled foods, nutritionally functional foods, quasi-drugs, etc. may also be mentioned. Among these, particularly, labels approved by the Consumer Affairs Agency, for example, labels or the like approved by systems for foods for specified health uses, systems for functionality labeled foods, and systems similar to these, may be mentioned. More specifically, labels for foods for specified health uses, labels for foods for conditional specified health uses, labels for functionality labeled foods, labels to the effect that the structure or function of a body is affected, labels on disease risk reduction, and the like may be mentioned. Among these, typical examples include labels for foods for specified health uses, which are stipulated in the Enforcement Regulations of Health Promotion Law (Apr. 30, 2003, Japanese Ministry of Health, Labor, and Welfare Ordinance No. 86) (particularly, labels for health applications), labels for functionality labeled foods, which are stipulated in Food Labeling Act (2013, Law No. 70), and labels similar thereto.

Modified Milk Powder

The nutritional composition according to the present technology may be properly used in foods/drinks, especially, in modified milk powder. As for the modified milk powder, modified milk powder for babies, modified milk powder for follow-up, modified milk powder for low birth weight infants, modified milk powder for children, modified milk powder for adults, modified milk powder for elderly, modified milk powder for allergy, modified milk powder for lactose intolerance, modified milk powder for inborn errors of metabolism and the like may be mentioned. Particularly, use for modified milk powder for babies, modified milk powder for follow-up, modified milk powder for low birth weight infants, and modified milk powder for children is desirable. The modified milk powder for babies refers to modified milk powder for babies, which targets 0 to 12-month-old babies, follow-up milk which targets babies after 6 to 9 months and young preschoolers (up to 3 years), modified milk powder for low birth weight infants, which targets newborn babies (low birth weight infants) weighing less than 2500 g at birth, various therapeutic milks used for treatment of children having pathological conditions such as milk allergy or lactose intolerance, or the like. Also, the corresponding composition may be applied to health functional foods or foods for patients. A health functional food system is provided for not only general foods but also foods in the form of tablets, capsules, etc., as targets, on the premise of domestic and foreign trends, and consistency with a traditional system for foods for specified health uses, and is composed of two types such as types of foods for specified health uses (individual permission type) and nutritionally functional foods (standard reference type).

When the nutritional composition of the present technology is administered, Bacteria of the genus *Bifidobacterium* and/or *lactobacilli* proliferate in the intestine of an administration subject. The proliferation of these probiotics in the intestine improves immunity, and further improves intestinal flora. In particular, in infants, when the nutritional composition of the present invention is administered, Bifidobacteria in the intestine are effectively increased, and the intestinal environment is improved. Also, by incorporating bad bacteria or opportunistic bacteria together with Bifidobacteria, immunity may be acquired, and the intestinal environment such as the entire intestinal bacteria flora, will be maintained, even when adulthood is reached.

As a method of producing modified milk powder, one type or two or more types of known production methods may be freely used in combination as long as the effect of the present technology is not decreased or inhibited. Specifically, for example, in the production, raw material milk may be mixed with the nutritional composition according to the present technology and various additives, and subjected to processes such as homogenization, sterilization, concentration, drying, granulation, and sieving.

Specifically, the modified milk powder of the present technology may be produced by, for example, the following method.

That is, the present technology provides a method of producing milk powder for enhancing a breast milk component, in which microbial cell powder, which includes bacteria belonging to *Bifidobacterium bifidum* and one or more types of probiotics having a low ability to assimilate human milk oligosaccharides, is mixed with human milk oligosaccharides to obtain milk powder for enhancing a breast milk component.

Specifically, there is provided a method of producing milk powder for enhancing a breast milk component, which includes the following steps (A) to (C):
(A) a step of culturing bacteria belonging to *Bifidobacterium bifidum*, and one or more types of probiotics having a low ability to assimilate human milk oligosaccharides in the present invention, in a medium containing a milk component to obtain cultures;
(B) a step of subjecting the cultures to spray-drying and/or freeze-drying to obtain respective microbial cell powders; and
(C) a step of mixing the microbial cell powders with human milk oligosaccharides to obtain modified milk powder.

Also, the present technology provides a method of producing modified milk powder, which includes the following step (A):
(A) a step of mixing human milk oligosaccharides, bacteria belonging to *Bifidobacterium bifidum*, one or more types of probiotics having a low ability to assimilate human milk oligosaccharides of the invention, and a milk component to obtain milk powder.

Also, specifically, the food composition of the present technology may be, for example, a supplement for babies. The supplement for babies may be produced by, for example, the following method.

That is, the present technology provides a method of producing a supplement for enhancing a breast milk component, which includes the following steps (A) and (B):
(A) a step of mixing human milk oligosaccharides, bacteria belonging to *Bifidobacterium bifidum*, one or more types of probiotics having a low ability to assimilate human milk oligosaccharides, and an excipient to obtain a mixture; and
(B) a step of tableting the mixture.

In any of the production methods, ingredients other than the ingredients mentioned in the above steps may be properly used in combination.

A method of adding the nutritional composition according to the present technology is not particularly limited as long as the effect of the present technology is not impaired, but, for example, the nutritional composition according to the present technology may be added in a liquid state at the time of mixing as described above, or may be added after formed into powder, and then powder-mixing may be performed for production.

The content of bacteria belonging to *Bifidobacterium bifidum* in the modified milk powder according to the present technology may be freely set as long as the effect of the present technology is not decreased or inhibited. In the present technology, in particular, the amount of bacteria belonging to *Bifidobacterium bifidum* in the modified milk powder may be set to $10^3$ to $10^{12}$ CFU/g with respect to the final composition of the modified milk powder.

The amount of probiotics having a low ability to assimilate human milk oligosaccharides in the modified milk powder according to the present technology may be freely set as long as the effect of the present technology is not decreased or inhibited. In the present technology, in particular, the amount of probiotics having a low ability to assimilate human milk oligosaccharides in the modified milk powder may be set to $10^3$ to $10^{12}$ CFU/g with respect to the final composition of the modified milk powder.

The amount of HMOs in the modified milk powder according to the present technology may be freely set as long as the effect of the present technology is not decreased or inhibited. In the present technology, in particular, the amount of HMOs in the modified milk powder may be set to 0.3% to 5.0% with respect to the final composition of the modified milk powder.

<Medicine, Quasi-Drug>

The nutritional composition according to the present technology may be added to a conventionally known medicine or quasi-drug (hereinafter, also referred to as a "medicine, etc.") in preparation, or may be mixed with raw materials of the medicine, etc. so as to produce a new medicine, etc.

When the nutritional composition according to the present technology is blended with the medicine, etc., the corresponding medicine, etc. may be properly formulated into a desired dosage form according to an administration method such as oral administration or parenteral administration. The dosage form is not particularly limited, but in the case of oral administration, it is possible to formulate, for example, solid preparations such as powder, granules, tablets, troches, and capsules; and liquid preparations such as solutions, syrups, suspensions, and emulsions. In the case of parenteral administration, it is possible to formulate, for example, suppositories, spray, inhalants, ointment, patches, injections, and the like. In the present technology, formulation of a dosage form for oral administration is preferred.

The formulation may be properly carried out according to a dosage form by a conventionally known method.

In the formulation, the formulation may be performed by properly blending with a formulation carrier. Also, in addition to the peptide of the present technology, components generally used for formulation, such as an excipient, a pH adjuster, a colorant, and a corrigent, may be used. Also, components having an effect of preventing, improving and/or treating diseases or symptoms which are conventionally known or to be found in the future may be properly used in combination depending on purposes.

As for the formulation carrier, various organic or inorganic carriers may be used depending on the dosage forms. In the case of solid preparations, examples of the carrier may include excipients, binders, disintegrants, lubricants, stabilizers, corrigents/flavoring agents, etc.

Examples of the excipient may include sugar derivatives such as lactose, sucrose, glucose, mannitol, and sorbitol; starch derivatives such as corn starch, potato starch, α-starch, dextrin, and carboxymethyl starch; cellulose derivatives such as crystalline cellulose, hydroxypropyl cellulose, hydroxypropyl methyl cellulose, carboxymethyl cellulose, and carboxymethyl cellulose calcium; gum arabic; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binder may include gelatin; polyvinylpyrrolidone; macrogol and the like, in addition to the excipients.

Examples of the disintegrant may include cellulose derivatives or chemically modified starch such as sodium croscarmellose, sodium carboxymethyl starch, and cross-linked polyvinylpyrrolidone, in addition to the excipients.

Examples of the lubricant may include talc; stearic acid; metallic stearates such as calcium stearate, and magnesium stearate; colloidal silica; waxes such as bee gum, and spermaceti; boric acid; glycol; carboxylic acids such as fumaric acid and adipic acid; carboxylic acid sodium salts such as sodium benzoate; sulfates such as sodium sulfate; leucine; lauryl sulfates such as sodium lauryl sulfate, and magnesium lauryl sulfate; silicic acids such as silicic acid anhydride, and silicic acid hydrate; and starch derivatives.

Examples of the stabilizer may include paraoxybenzoic acid esters such as methylparaben and propylparaben; alcohols such as chlorobutanol, benzyl alcohol, and phenylethyl alcohol; benzalkonium chloride; acetic anhydride; and sorbic acid.

Examples of the corrigent/flavoring agent may include sweeteners, acidulants, flavors, etc.

As for the carrier to be used in the case of liquid preparations for oral administration, a solvent such as water, a corrigent/flavoring agent, etc. may be mentioned.

The amount of bacteria belonging to *Bifidobacterium bifidum* in the medicine, etc. according to the present technology may be freely set as long as the effect of the present technology is not decreased or inhibited. In the present technology, in particular, the amount of bacteria belonging to *Bifidobacterium bifidum* in the medicine, etc. may be set to $10^3$ to $10^{12}$ CFU/mL or g with respect to the final composition of the medicine, etc.

The amount of probiotics having a low ability to assimilate human milk oligosaccharides in the medicine, etc. according to the present technology may be freely set as long as the effect of the present technology is not decreased or inhibited. In the present technology, in particular, the content of probiotics having a low ability to assimilate human milk oligosaccharides in the medicine, etc. may be set to $10^3$ to $10^{12}$ CFU/mL or g with respect to the final composition of the medicine, etc.

The amount of HMOs in the medicine, etc. according to the present technology may be freely set as long as the effect of the present technology is not impaired. In the present technology, in particular, the amount of HMOs in the medicine, etc. may be set to 0.3% to 5.0% with respect to a final composition of the medicine, etc.

<Feed>

The nutritional composition according to the present technology may be added to a conventionally known feed in preparation, or may be mixed with raw materials of the feed so as to produce a new feed.

When the nutritional composition according to the present technology is blended with the feed, examples of raw materials of the feed may include cereals such as corn, wheat, barley, and rye; brans such as wheat bran, barley bran, rice bran, and defatted rice bran; by-product feeds such as corn gluten meal and corn germ meal; animal feeds such as skim milk powder, whey, fish meal, and bone meal; yeasts such as beer yeast; mineral feeds such as calcium phosphate, and calcium carbonate; oils and fats; amino acids; and sugars. Also, examples of the form of the feed may include pet feeds (pet foods and the like), livestock feeds, fish feeds, and the like.

The amount of bacteria belonging to *Bifidobacterium bifidum* in the feed according to the present technology may be freely set according to the body weight, etc. as long as the effect of the present technology is not decreased or inhibited. In the present technology, in particular, the amount of bacteria belonging to *Bifidobacterium bifidum* in the feed may be set to $10^3$ to $10^{12}$ CFU/mL or g with respect to the final composition of the feed.

The amount of probiotics having a low ability to assimilate human milk oligosaccharides in the feed according to the present technology may be freely set according to the body weight, etc. as long as the effect of the present technology is not decreased or inhibited. In the present technology, in particular, the amount of probiotics having a low ability to assimilate human milk oligosaccharides in the feed may be set to $10^3$ to $10^{12}$ CFU/mL or g with respect to the final composition of the feed.

The amount of HMOs in the feed according to the present technology may be freely set according to the body weight, etc. as long as the effect of the present technology is not decreased or inhibited. In the present technology, in particular, the content of HMOs in the feed may be set to 0.3% to 5.0% with respect to the final composition of the feed.

The present technology may also employ the following configurations.

[1] A nutritional composition containing:
bacteria belonging to *Bifidobacterium bifidum*;
one or more types of probiotics having a low ability to assimilate human milk oligosaccharides; and
human milk oligosaccharides.

[2] A food/drink composition containing:
bacteria belonging to *Bifidobacterium bifidum*;
one or more types of probiotics having a low ability to assimilate human milk oligosaccharides; and
human milk oligosaccharides.

[3] Modified milk powder containing:
bacteria belonging to *Bifidobacterium bifidum*;
one or more types of probiotics having a low ability to assimilate human milk oligosaccharides; and
human milk oligosaccharides.

[4] A medicine or quasi-drug composition containing:
bacteria belonging to *Bifidobacterium bifidum*;
one or more types of probiotics having a low ability to assimilate human milk oligosaccharides; and
human milk oligosaccharides.

[5] A feed composition containing:
bacteria belonging to *Bifidobacterium bifidum*;
one or more types of probiotics having a low ability to assimilate human milk oligosaccharides; and
human milk oligosaccharides.

[6] Use of bacteria belonging to *Bifidobacterium bifidum*, one or more types of probiotics having a low ability to assimilate human milk oligosaccharides, and human milk oligosaccharides, in a nutritional composition.

[7] Use of bacteria belonging to *Bifidobacterium bifidum*, one or more types of probiotics having a low ability to assimilate human milk oligosaccharides, and human milk oligosaccharides, in a food/drink composition.

[8] Use of bacteria belonging to *Bifidobacterium bifidum*, one or more types of probiotics having a low ability to assimilate human milk oligosaccharides, and human milk oligosaccharides, in modified milk powder.

[9] Use of bacteria belonging to *Bifidobacterium bifidum*, one or more types of probiotics having a low ability to assimilate human milk oligosaccharides, and human milk oligosaccharides, in a medicine or quasi-drug composition.

[10] Use of bacteria belonging to *Bifidobacterium bifidum*, one or more types of probiotics having a low ability to assimilate human milk oligosaccharides, and human milk oligosaccharides, in a feed composition.

[11] Use of bacteria belonging to *Bifidobacterium bifidum*, one or more types of probiotics having a low ability to assimilate human milk oligosaccharides, and human milk oligosaccharides, in producing a nutritional composition.

[12] Use of bacteria belonging to *Bifidobacterium bifidum*, one or more types of probiotics having a low ability to assimilate human milk oligosaccharides, and human milk oligosaccharides, in producing a food/drink composition.

[13] Use of bacteria belonging to *Bifidobacterium bifidum*, one or more types of probiotics having a low ability to assimilate human milk oligosaccharides, and human milk oligosaccharides, in producing modified milk powder.

[14] Use of bacteria belonging to *Bifidobacterium bifidum*, one or more types of probiotics having a low ability to assimilate human milk oligosaccharides, and human milk oligosaccharides, in producing a medicine or quasi-drug composition.

[15] Use of bacteria belonging to *Bifidobacterium bifidum*, one or more types of probiotics having a low ability to assimilate human milk oligosaccharides, and human milk oligosaccharides, in producing a feed composition.

[16] In [1] to [15],
the human milk oligosaccharides are 2'-fucosyllactose and/or lacto-N-neotetraose.

[17] In [1] to [16],
the probiotics are bacteria of the genus *Bifidobacterium* (excluding the bacteria belonging to *Bifidobacterium bifidum*) and/or *lactobacilli*.

[18] In [17],
the bacteria of the genus *Bifidobacterium* (excluding the bacteria belonging to *Bifidobacterium bifidum*) are at least one bacterium selected from *Bifidobacterium longum* subspecies *longum*, *Bifidobacterium adolescentis*, *Bifidobacterium pseudocatenulatum*, *Bifidobacterium animalis* subspecies *lactis*, *Bifidobacterium breve*, and *Bifidobacterium pseudolongum*.

[19] In [17],
the *lactobacilli* are at least one bacterium selected from *Lactobacillus paracasei*, *Lactobacillus plantarum*, *Lactobacillus acidophilus*, *Lactobacillus rhamnosus*, and *Lactobacillus gasseri*.

[20] In [1] to [19],
the bacteria belonging to *Bifidobacterium bifidum* are at least one bacterium selected from *Bifidobacterium bifidum* ATCC29521, *Bifidobacterium bifidum* (NITE BP-02429), *Bifidobacterium bifidum* (NITE BP-1252), *Bifidobacterium bifidum* (NITE BP-02431), *Bifidobacterium bifidum* (NITE BP-02648), *Bifidobacterium bifidum* (NITE BP-02432), and *Bifidobacterium bifidum* (NITE BP-02433).

[21] A method of producing modified milk powder, which includes the following steps (A) to (C).
(A) a step of culturing bacteria belonging to *Bifidobacterium bifidum*, and one or more types of probiotics having a low ability to assimilate human milk oligosaccharides, in a medium containing a milk component to obtain cultures;
(B) a step of subjecting the cultures to spray-drying and/or freeze-drying to obtain respective microbial cell powders; and
(C) a step of mixing the microbial cell powders with human milk oligosaccharides to obtain modified milk powder.

[22] A method of producing modified milk powder, which includes the following step (A):
(A) a step of mixing human milk oligosaccharides, bacteria belonging to *Bifidobacterium bifidum*, one or more types of probiotics having a low ability to assimilate human milk oligosaccharides, and a milk component to obtain milk powder.

[23] A method of producing a supplement for enhancing a breast milk component, which includes the following steps (A) and (B).
(A) a step of mixing human milk oligosaccharides, bacteria belonging to *Bifidobacterium bifidum*, one or more types of probiotics having a low ability to assimilate human milk oligosaccharides, and an excipient to obtain a mixture; and
a step of tableting the mixture.

[24] In the method described in [21] or [22], the milk component is a milk protein.

[25] In the method described in [24], the milk protein is at least one component selected from the group including whey, whey hydrolysate, and casein.

[26] A method of producing a supplement, which includes the following steps (A) and (B):
(A) a step of mixing bacteria of the genus *Bifidobacterium*, and an excipient to obtain a mixture; and
a step of tableting the mixture.

[27] In [21] to [26],
the human milk oligosaccharides are 2'-fucosyllactose and/or lacto-N-neotetraose.

[28] In [21] to [27],
the probiotics are Bacteria of the genus *Bifidobacterium* (excluding the bacteria belonging to *Bifidobacterium bifidum*) and/or *lactobacilli*.

[29] In [28],
the bacteria of the genus *Bifidobacterium* (excluding the bacteria belonging to *Bifidobacterium bifidum*) are at least one bacterium selected from *Bifidobacterium longum* subspecies *longum*, *Bifidobacterium adolescentis*, *Bifidobacterium pseudocatenulatum*, *Bifidobacterium animalis* subspecies *lactis*, *Bifidobacterium breve*, and *Bifidobacterium pseudolongum*.

[30] In [28],
the *lactobacilli* are at least one bacterium selected from *Lactobacillus paracasei*, *Lactobacillus plantarum*, *Lactobacillus acidophilus*, *Lactobacillus rhamnosus*, and *Lactobacillus gasseri*.

[31] In [21] to [30], in the nutritional composition described in any one of claims 1 to 5,
the bacteria belonging to *Bifidobacterium bifidum* are at least one bacterium selected from *Bifidobacterium bifidum* ATCC29521, *Bifidobacterium bifidum* (NITE BP-2429), *Bifidobacterium bifidum* (NITE BP-1252), *Bifidobacterium bifidum* (NITE BP-2431), *Bifidobacterium bifidum* (NITE BP-02648), *Bifidobacterium bifidum* (NITE BP-02432), and *Bifidobacterium bifidum* (NITE BP-02433).

EXAMPLES

Hereinafter, the present technology will be described on the basis of Examples in more detail. Examples described below are described as examples of a representative Example of the present technology, by which the scope of the present technology is not to be narrowly construed.

Experimental Method (1) Preparation of Sugar Solution

A 10% solution of glucose (manufactured by Nakarai Tesque Inc.), and 2'-FL ((≥95%) Funakoshi, available from sigma), and LNnT (manufactured by ELICITYL) as examples of HMOs was prepared with ion exchanged water, and was subjected to sterile filtration using Millex-GV (SLGV033RS).

(2) Bacterial Solution Preparation of Bacteria of the Genus *Bifidobacterium* and *Lactobacilli*

*Lactobacilli* MRS Broth (BD) (0.05% L-Cysteine Hydrochloride for Bacteria of the genus *Bifidobacterium*) was added to strains of Table 1 below (bacteria belonging to *Bifidobacterium bifidum*) and Table 2 below. After a sterilization treatment, 3% of the bacterial solution was inoculated, and anaerobically cultured (pre-pre cultured) at 37° C. for 16 h.

The following day, 1% glucose was added to a modified BL agar medium ("Studies on Bifidobacteria" by Tomotari Mitsuoka, p. 306, Japan *Bifidus* Foundation, issued in 1994) noted in Table 3, for preparation. After a sterilization treatment, 3% of the pre-pre cultured bacterial solution was inoculated, and anaerobically pre-cultured (pre-cultured) at 37° C. for 12 h.

The pre-cultured bacterial solution was collected and washed once with a sterile physiological saline solution. Then, mass-up was performed to an equal volume with the modified BL agar medium ("Studies on Bifidobacteria" by Tomotari Mitsuoka, p. 306, Japan *Bifidus* Foundation, issued in 1994) noted in Table 3 to prepare a suspended bacterial solution.

(3) Preparation of Medium for Analysis of the Number of Proliferating Bacteria in Bacteria of the Genus *Bifidobacterium* and *Lactobacilli*

The modified BL agar medium ("Studies on Bifidobacteria" by Tomotari Mitsuoka, p. 306, Japan *Bifidus* Foundation, issued in 1994) noted in Table 3 was prepared at a capacity of 60%, and was subjected to an autoclave sterilization treatment. Then, 40% of each sugar solution prepared in (1) was aseptically added so as to prepare a medium with a sugar concentration of 4%.

(4) Single Bacterial Culturing of Strains of Table 1 Below and Table 2 Below

The medium prepared in the above (3) was dispensed at a capacity that is half the capacity for culturing in a 96-well plate, and the bacterial solution prepared in the above (2) was dispensed at a remaining half capacity such that the bacterial solution had 6%. Then, a final sugar concentration was set to 2%. The plate into which the bacterial solution was dispensed was anaerobically cultured at 37° C. for 8 h.

(5) Mix-Culturing of Bacteria Belonging to *Bifidobacterium bifidum* and Probiotics Having Low Ability to Assimilate Human Milk Oligosaccharides The medium prepared in the above (3) was dispensed at a capacity that is half the capacity for aseptic culturing in a 96-well plate, and each of the bacterial solutions of strains of bacteria belonging to *Bifidobacterium bifidum* in Table 1 and probiotics having a low ability to assimilate human milk oligosaccharides in Table 2, which was prepared in the above (2), was dispensed at a remaining quarter capacity into the medium prepared in the above (3) such that the bacterial solution had 12%. Then, a final sugar concentration was set to 2%. The plate into which the bacterial solution was dispensed was anaerobically cultured at 37° C. for 8 h.

(6) Method of Analyzing the Number of Proliferating Bacteria in Bacteria of the genus *Bifidobacterium* and *Lactobacilli*

OD650 was measured from each well in the plates in the above (4) and the above (5) before (0 h) culturing and after (8 h) culturing, by MICROPLATE READER SH-9000 (manufactured by CORONA ELECTRIC). After turbidity measurement, microbial cells were collected, and DNA extraction was performed. After the DNA extraction, the number of proliferating bacteria of Bifidobacteria/*lactobacilli* was analyzed by using the bacterial species-specific primer noted in Table 4, by a quantitative PCR method (see "Structural analysis of intestinal flora"—analysis of bacterial flora in human feces using quantitative PCR—by Kouichi Watanabe, Enterobacteriological journal, 20:35-42, 2006).

Table 1:

TABLE 1

| Bacteria belonging to *Bifidobacterium bifidum* | |
|---|---|
| Strain | |
| *Bifidobacterium bifidum* | ATCC29521[T] |
| *Bifidobacterium bifidum* | NITE BP-02429 |
| *Bifidobacterium bifidum* | NITE BP-1252 |
| *Bifidobacterium bifidum* | NITE BP-02431 |
| *Bifidobacterium bifidum* | NITE P-02648 |
| *Bifidobacterium bifidum* | NITE BP-02432 |
| *Bifidobacterium bifidum* | NITE BP-02433 |

T: type strain

TABLE 2

Table 2: Bacteria used in Examples except for *Bifidobacterium bifidum*

| | Strain |
|---|---|
| *Bifidobacterium longum* subsp *longum* | ATCC15707[T] |
| *Bifidobacterium longum* subsp *longum* | BB536 |
| *Bifidobacterium longum* subsp *infantis* | ATCC15697[T] |
| *Bifidobacterium breve* | ATCC15700[T] |
| *Bifidobacterium adolescentis* | ATCC15703[T] |
| *Bifidobacterium peseudocatenulatum* | ATCC27919[T] |
| *Bifidobacterium pseudolongum* | ATCC25526[T] |
| *Bifidobacterium animalis* subsp *lactis* | DSM10140[T] |
| *Bifidobacterium animalis* subsp *lactis* | MCC-525 |
| *Lactobacillus paracasei* | ATCC25302[T] |
| *Lactobacillus plantarum* | ATCC14917[T] |
| *Lactobacillus acidophhilus* | ATCC4356[T] |
| *Lactobacillus rhamnosus* | ATCC7469[T] |
| *Lactobacillus gasseri* | ATCC33323[T] |

T: type strain

TABLE 3

Table 3: Modified BL agar medium

| | |
|---|---|
| 'LAB-LEMCO' POWDER(Oxoid) | 2.4 g |
| Bacto Proteose Peptone No. 3(BD) | 10.0 g |
| BBL Trypticase Peptone(BD) | 5.0 g |
| BBL Phytone Peptone(BD) | 3.0 g |
| Bacto Yeast extract(BD) | 5.0 g |
| Liver extract | 150.0 mL |
| Soluble starch(MERCK) | 0.5 g |
| Solution A | 10.0 mL |
| Solution B | 5.0 mL |
| Tween 80 (KANTO CHEMICAL) | 1.0 g |
| L-Cysteine Hydrochloride (KANTO CHEMICAL) | 0.5 g |
| pH 7.2 | |

Production method of liver extract: 10 g of Bacto Liver (BD), in 170 mL of purified water, is leached for about 1 h in a hot bath of 50 to 60° C., heated at 100° C. for several minutes, and filtered through filter paper after pH is corrected to 7.2.
Preparation method of solution A: 25 g of $KH_2PO_4$ and 25 g of $K_2HPO_4$ are dissolved in 250 mL of purified water
Preparation method of solution B: 10 g of $MgSO_4 \cdot 7H_2O$, 0.5 g of $FeSO_4 \cdot 7H_2O$, 0.5 g of NaCl, and 0.337 g of $MnSO_4$ are dissolved in 250 mL of purified water

TABLE 4

Table 4: Strain specific-oligo nucleotide primer Literature

| Species | Amplicon | Forward primer | Reverse primer | Literature |
|---|---|---|---|---|
| Bifidobacterium bifidum | 278 | CCACATGATCGCATGTGATTG | CCGAAGGCTTGCTCCCAAA | Matsuki T, et al. 1998 |
| Bifidobacterium longum subsp longum | 831 | TTCCAGTTGATCGCATGGTC | GGGAAGCCGTATCTCTACGA | Matsuki T, et al. 1998 |
| Bifidobacterium adlescentis | 279 | CTCCAGTTGGATGCATGTC | CGAAGGCTTGCTCCCAGT | Matsuki T, et al. 1998 |
| Bifidobacterium catenulatum group | 289 | CGGATGCTCCGACTCCT | CGAAGGCTTGCTCCCGAT | Matsuki T, et al. 1998 |
| Bifidobacterium Pseudolongum | 297 | CACATGAGCGCATGCGAG | TCCACTCAACACGGCCGAA | Matsuki T, et al. 1998 |
| Bifidobacterium animalis subsp lactis | 680 | GTGGAGACACGGTTTCCC | CACACCACACAATCCAATAC | M. Ventura, et. al. 2001 |
| Lactobacillus casei | 327 | CGAGTTCTCGTTGATGATC | AAGATTCCCTACTGCTGCC | Watanabe K, et al. 1998 |
| Lactobacillus plantarum | 250 | AGATTTGATCATGGCTCAG | CGGTATTAGCATCTGTTTCC | F. Quere, et. al. 1997 |
| Lactobacillus acidophilus | 420 | ACAGATTCACTTCGGTG | AAAGGCCAGTTACTACCTCTATC | Watanabe K, et al. 1998 |
| Lactobacillus rhamnosus | 446 | GCAAGTCGAACGAGTTCTGATTAT | GCCGACAACAGTTACTCTGCCGACCA | Watanabe K, et al. 1998 |
| Lactobacillus gasseri | 319 | GATGAATTTGGTGCTTGCACCAG | AAGATTCCCTACTGCTGCC | Watanabe K, et al. 1998 |

<Measurement Results>
(1) Availability of HMOs by Bacteria Belonging to *Bifidobacterium bifidum*

Regarding bacteria belonging to *Bifidobacterium bifidum* in Table 1, each strain was cultured as a single bacterium by 2'-FL or LNnT (HMOs) as a sugar source, and OD650 was measured. The results are noted in Table 5 below. Table 5 illustrates OD650 increase values after seven strains of the bacteria belonging to *Bifidobacterium bifidum* in Table 1 were cultured for 8 h by 2'-FL or LNnT as a sugar source.

TABLE 5

Table 5: OD650 increase value

|  | ATCC 29521$^T$ | NITE BP-02429 | NITE BP-1252 | NITE BP-02431 | NITE P-02648 | NITE BP-02432 | NITE BP-02433 |
|---|---|---|---|---|---|---|---|
| 2'-FL | 0.060 | 0.167 | 0.225 | 0.037 | 0.470 | 0.430 | 0.431 |
| LNnT | 0.008 | 0.608 | 0.373 | 0.535 | 0.719 | 0.522 | 0.370 |

T: type strain

As illustrated in Table 5, all the bacteria belonging to *Bifidobacterium bifidum* in Table 1 had assimilability of 2'-FL or LNnT (HMOs).

(2) Availability of HMOs by Probiotics Having Low Ability to Assimilate Human Milk Oligosaccharides Regarding strains in Table 2, each strain was cultured as a single bacterium by 2'-FL or LNnT (HMOs) as a sugar source, and OD650 was measured. The results for 2'-FL are noted in Table 6 below, and the results for LNnT are noted in Table 7 below.

TABLE 6

Table: 6 OD650 Increase value

|  | NITE BP-02429 (PC) | ATCC 157007 | ATCC 15707$^T$ | ATCC 156971 | ATCC 15703$^T$ | ATCC 27919$^T$ | ATCC 25526$^T$ |
|---|---|---|---|---|---|---|---|
| 2'-FL | 0.135 | 0.041 | 0.029 | 0.344 | −0.01 | 0.02 | 0.022 |

|  | DSM 101407 | ATCC 25302$^T$ | ATCC 4356$^T$ | ATCC 14917$^T$ | ATCC 7469$^T$ | ATCC 33323$^T$ |
|---|---|---|---|---|---|---|
| 2'-FL | 0.027 | −0.011 | 0.01 | 0.013 | 0.058 | −0.017 |

T: type strain

TABLE 7

Table 7: OD650 increase value

|  | NITE BP-02429 (PC) | BB536 | MCC-525 | ATCC 25302$^T$ |
|---|---|---|---|---|
| LNnT | 0.608 | 0.053 | 0.096 | 0.052 |

P C: positive control
T: type strain

As illustrated in Tables 6 and 7, among strains in Table 2, all the strains except for *Bifidobacterium infantis* which is considered to have availability, had no assimilability in 2'-FL or LNnT (HMOs), or a low assimilability.

(3) Mix-Culturing of Bacteria Belonging to *Bifidobacterium bifidum* and Probiotics Having Low Ability to Assimilate Human Milk Oligosaccharides by HMOs as Sugar Source

*Bifidobacterium bifidum* (NITE BP-02429)+Probiotics Having Low Ability to Assimilate Human Milk Oligosaccharides It was decided to culture *Bifidobacterium bifidum* (NITE BP-02429) in which availability of 2'-FL or LNnT was found as described above, in combination with strains in Table 2, which cannot use 2'-FL or LNnT. *Bifidobacterium bifidum* (NITE BP-02429) and the strains in Table 2, which cannot use 2'-FL or LNnT, were mix-cultured by 2'-FL or LNnT as a sugar source, and after culturing for 8 h, the proliferation rate of the number of bacteria of each strain (proliferation rate=the number of bacteria after mix-culturing for 8 h/the number of bacteria after single bacterial culturing) was measured by a quantitative PCR method using each strain-specific oligonucleotide primer noted in Table 4, for the strain in Table 2. The results are noted in Table 8.

TABLE 8

Table 8: Proliferation rate

| | BB536 | ATCC 15703[T] | ATCC 27919[T] | ATCC 25526[T] | MCC-525 | ATCC 25302[T] | ATCC 14917[T] | ATCC 4356[T] | ATCC 7469[T] | ATCC 33323[T] |
|---|---|---|---|---|---|---|---|---|---|---|
| 2'-FL | 4.30 | 1.91 | 3.08 | 1.24 | 2.62 | 6.92 | 1.76 | 3.54 | 2.69 | 3.70 |
| LNnT | 2.13 | 1.53 | 1.55 | 0.98 | 1.41 | 4.23 | 2.58 | 3.77 | 5.03 | 1.53 |

T: type strain

As illustrated in Table 8, it was found that even a strain having no assimilability in human milk oligosaccharides in Table 6 or 7 proliferates through mix-culturing with *Bifidobacterium bifidum* (NITE BP-02429).

Bacteria Belonging to *Bifidobacterium Bifidum+Bifidobacterium Longum* Subspecies *Longum* BB536

Seven strains of *Bifidobacterium bifidum* in Table 1 and *Bifidobacterium longum* subspecies *longum* BB536 which cannot use 2'-FL or LNnT were mix-cultured by 2'-FL or LNnT as a sugar source. The number of bacteria of *Bifidobacterium longum* subspecies *longum* BB536 after culturing for 8 h, and the number of bacteria after 8 h of single bacterial culturing were measured by a quantitative PCR method using *Bifidobacterium longum* subspecies *longum*-specific oligo nucleotide primer noted in Table 4, and proliferation rates (proliferation rate=the number of mix-cultured bacteria after 8 h/the number of bacteria in 8 h of single bacterial culturing) were compared. The results are noted in Table 9.

TABLE 9

Table 9: Proliferation rate

| | ATCC 29521[T] | NITE BP-02429 | NITE BP-1252 | NITE BP-02431 | NITE P-02648 | NITE BP-02432 | NITE BP-02433 |
|---|---|---|---|---|---|---|---|
| 2'-FL | 1.35 | 4.13 | 3.17 | 6.33 | 9.97 | 3.16 | 5.90 |
| LNnT | 1.07 | 3.57 | 1.64 | 3.02 | 4.95 | 1.51 | 3.08 |

T: type strain

As illustrated in Table 9, it was found that *Bifidobacterium longum* subspecies *longum* BB536 having no assimilability of 2'-FL proliferates through mix-culturing with bacteria belonging to *Bifidobacterium bifidum*. Also, it was found that *Bifidobacterium longum* subspecies *longum* BB536 having no assimilability of LNnT proliferates through mix culturing with bacteria belonging to *Bifidobacterium bifidum*.

Bacteria Belonging to *Bifidobacterium bifidum+Bifidobacterium Animalis* Subspecies *Lactis* MCC-525

Seven strains of *Bifidobacterium bifidum* in Table 1 and *Bifidobacterium animalis* subspecies *lactis* MCC-525 which cannot use 2'-FL or LNnT were mix-cultured by 2'-FL or LNnT as a sugar source. The number of bacteria of *Bifidobacterium animalis* subspecies *lactis* MCC-525 after culturing for 8 h, and the number of bacteria after 8 h of single bacterial culturing were measured by a quantitative PCR method using *Bifidobacterium animalis* subspecies *lactis*-specific oligo nucleotide primer in Table 4, and proliferation rates (proliferation rate=the number of mix-cultured bacteria after 8 h/the number of bacteria in 8 h of single bacterial culturing) were compared. The results are noted in Table 10.

Table 10:

TABLE 10

| | Proliferation rate | | | | | | |
|---|---|---|---|---|---|---|---|
| | ATCC 29521[T] | NITE BP-02429 | NITE BP-1252 | NITE BP-02431 | NITE P-02648 | NITE BP-02432 | NITE BP-02433 |
| 2'-FL | 2.01 | 4.85 | 2.06 | 3.82 | 4.35 | 2.45 | 3.67 |
| LNnT | 3.87 | 4.17 | 19.98 | 3.58 | 6.03 | 4.21 | 2.39 |

T: type strain

In all combinations with *Bifidobacterium bifidum*, it was found that when *Bifidobacterium animalis* subspecies *lactis* MCC-525 was cultured in combination with seven strains of *Bifidobacterium bifidum* by 2'-FL or LNnT as a sugar source, the number of proliferating bacteria was promoted as compared to that in a case where *Bifidobacterium animalis* subspecies *lactis*MCC-525 was cultured as a single bacterium. Among them, in the combination with *Bifidobacterium bifidum* (NITE BP-1252), the proliferation promotion effect of the number of bacteria was significantly higher as compared to when LNnT was set as a sugar source.

Bacteria Belonging to *Bifidobacterium bifidum*+*Lactobacillus Gasseri* ATCC33323

Seven strains of *Bifidobacterium bifidum* in Table 1 and *Lactobacillus gasseri* ATCC 33323$^T$ which cannot use 2'-FL were mix-cultured by 2'-FL as a sugar source. The number of bacteria of *Lactobacillus gasseri* ATCC 33323$^T$ after 8 h, and the number of bacteria after 8 h of single bacterial culturing were measured by a quantitative PCR method using *Lactobacillus gasseri* specific-oligo nucleotide primer in Table 4, and proliferation rates (proliferation rate=the number of mix-cultured bacteria after 8 h/the number of bacteria in 8 h of single bacterial culturing) were compared. The results are noted in Table 11.

Table 11:

TABLE 11

| | proliferation rate | | | | | | |
|---|---|---|---|---|---|---|---|
| | ATCC 29521$^T$ | NITE BP-02429 | NITE BP-1252 | NITE BP-02431 | NITE P-02648 | NITE BP-02432 | NITE BP-02433 |
| 2'-FL | 1.45 | 2.33 | 3.99 | 4.42 | 2.88 | 3.99 | 3.64 |

T: type strain

In all combinations, it was found that when *Lactobacillus gasseri* ATCC33323T was cultured in combination with seven strains of *Bifidobacterium bifidum* by 2'-FL as a sugar source, the number of proliferating bacteria was promoted as compared to the number of bacteria in a case where *Lactobacillus gasseri* ATCC33323$^T$ was cultured as a single bacterium. Among seven strains of *Bifidobacterium bifidum*, the proliferation effect was higher in six strains other than *Bifidobacterium bifidum* ATCC29521$^T$.

Bacteria Belonging to *Bifidobacterium bifidum*+*Lactobacillus Paracasei* ATCC 25302$^T$ Seven strains of *Bifidobacterium bifidum* in Table 1 and *Lactobacillus paracasei* ATCC 25302$^T$ which cannot use 2'-FL or LNnT were mix-cultured by 2'-FL or LNnT as a sugar source. After 8 h, the proliferation rate of the number of bacteria of *Lactobacillus paracasei* ATCC 25302$^T$, with respect to the number of bacteria after single bacterial culturing (proliferation rate=the number of mix-cultured bacteria after 8 h/the number of bacteria in 8 h of single bacterial culturing) was measured by a quantitative PCR method. The results are noted in Table 12.

TABLE 12

| Table 12: Proliferation ratio | | | | | | | |
|---|---|---|---|---|---|---|---|
| | ATCC 29521$^T$ | NITE BP-02429 | NITE BP-1252 | NITE BP-02431 | NITE P-02648 | NITE BP-02432 | NITE BP-02433 |
| 2'-FL | 2.28 | 4.21 | 1.98 | 3.25 | 4.23 | 2.01 | 3.23 |
| LNnT | 4.26 | 8.04 | 9.18 | 10.10 | 14.78 | 8.76 | 8.85 |

T: type strain

In all combinations, it was found that when *Lactobacillus paracasei* ATCC 25302$^T$ was cultured in combination with seven strains of *Bifidobacterium bifidum* by 2'-FL or LNnT as a sugar source, the number of proliferating bacteria was promoted as compared to that in a case where *Lactobacillus paracasei* ATCC 25302$^T$ was cultured as a single bacterium.

PRODUCTION EXAMPLE

Hereinafter, Production Examples of a nutritional composition, a medicine composition, and a food composition will be described.

Production Example 1

*Bifidobacterium bifidum* is added to 3 mL of MRS liquid medium, and is anaerobically cultured at 37° C. for 16 h. Then, the culture solution is concentrated, and freeze-dried to obtain freeze-dried powder of bacteria (bacterial powder). The bacterial powder containing *Bifidobacterium bifidum* is uniformly mixed with probiotics/human milk oligosaccharides (available from Funakoshi)/whey protein concentrate (WPC), and prebiotics (lactulose, raffinose and galactooligosaccharides) to obtain a composition. 20 g of the corresponding composition is dissolved in 200 g of water so as to obtain a nutritional composition.

Production Example 2

*Bifidobacterium bifidum* is added to 3 mL of MRS liquid medium, and is anaerobically cultured at 37° C. for 16 h. Then, the culture solution is concentrated, and freeze-dried to obtain freeze-dried powder of bacteria (bacterial powder). The bacterial powder is uniformly mixed with probiotics/human milk oligosaccharides (available from Funakoshi)/dry powder of a milk protein concentrate (MPC480, manufactured by Fonterra, protein content 80% by mass, casein protein:whey protein=about 8:2), and prebiotics (lactulose, raffinose and galactooligosaccharides). 20 g of the corresponding composition is dissolved in 200 g of water to obtain a nutritional composition.

Production Example 3

*Bifidobacterium bifidum* is added to 3 mL of MRS liquid medium, and is anaerobically cultured at 37° C. for 16 h. Then, the culture solution is concentrated, and freeze-dried to obtain freeze-dried powder of bacteria (bacterial powder). Then, the bacterial powder containing *Bifidobacterium bifidum*, probiotics/human milk oligosaccharides (available from Funakoshi)/prebiotics (lactulose, raffinose and galactooligosaccharides), and crystalline cellulose are put into a stirring granulator and mixed. Then, granulation is performed with addition of purified water, and the granulated product is dried. Then, the granulated product (a medicine composition) that contains an extract component of bacteria and pre/probiotics, and contains an excipient is obtained.

Production Example 4

A method of producing fermented milk to which *Bifidobacterium bifidum* is added will be described below.

First, a milk raw material is mixed with water, other components, or the like as necessary, and is preferably subjected to a homogenization treatment and a heat-sterilization treatment. The homogenization treatment and the heat-sterilization treatment may be performed by conventional methods. A *lactobacilli* starter is added (inoculated) to the sterilized milk preparation obtained through heat-sterilization, and fermentation is performed while a predetermined fermentation temperature is maintained, so that a fermented product is obtained. By the fermentation, curds are formed.

As for the *lactobacilli* starter, for example, *lactobacilli* generally used for yogurt production, such as *Lactobacillus bulgaricus, Lactococcus lactis*, and *Streptococcus thermophilus* may be used. When pH reaches a target value, the formed curds are crushed by stirring, and cooled to 10° C. or less to obtain a fermented product. By cooling to 10° C. or less, the activation of *lactobacilli* may be reduced and the production of acid may be suppressed.

Then, the fermented product obtained through the fermentation process is subjected to heat treatment to obtain a heated fermented product (a heat-treated fermented product). By properly heating the fermented product, it is possible to suppress acid from being produced by *lactobacilli* in the heated fermented product. Accordingly, during the subsequent production process and/or during storage of concentrated fermented milk containing Bifidobacteria, reduction of pH may be suppressed, and as a result, the viability of Bifidobacteria may be improved.

Next, *Bifidobacterium bifidum* and human milk oligosaccharides (available from Funakoshi) are added to the heated fermented product obtained through the heat treatment process. The addition amount of *Bifidobacterium breve* MCC1274 (FERM BP-11175) is preferably $1\times10^7$ to $1\times10^{11}$ CFU/mL, more preferably $1\times10^8$ to $1\times10^{10}$ CFU/mL with respect to the heated fermented product. When the *Bifidobacterium bifidum* are dead cells, CFU/mL may be replaced with individual cells/mL.

After *Bifidobacterium bifidum* and human milk oligosaccharides are added to the heated fermented product, concentration is performed. The concentration process may be performed by properly using a conventionally known concentration method. In the centrifugal separation method, whey in the concentration target (the heated fermented product to which Bifidobacteria and prebiotics are added) is removed to obtain concentrated fermented milk of *Bifidobacterium bifidum* in which the solid content concentration is increased. Ingestion of the obtained fermented milk makes it possible to improve intestinal flora.

Production Example 5

A method of producing modified milk powder to which *Bifidobacterium bifidum* is added will be described below.

10 kg of desalted milk whey protein powder (manufactured by Mirai), 6 kg of milk casein powder (manufactured by Fonterra), 48 kg of lactose (manufactured by Mirai), 920 g of a mineral mixture (manufactured by Tomita Pharmaceutical Co., Ltd.), 32 g of a vitamin mixture (manufactured by Tanabe Seiyaku Co., Ltd.), human milk oligosaccharides, 500 g of lactulose (manufactured by Morinaga Milk Industry Co., Ltd.), 500 g of raffinose (manufactured by Nippon Beet Sugar Manufacturing Co., Ltd.), and 900 g of galactooligosaccharide liquid sugar (manufactured by Yakult Pharmaceutical Industry Co., Ltd.) are dissolved in 300 kg of warm water, and then dissolved at 90° C. for 10 min through heating, and homogenized with addition of 28 kg of prepared fat (manufactured by Taiyo Yushi Corp.). Then, sterilization, and concentration steps are performed, and about 95 kg of modified milk powder is prepared through spray-drying. To this, 100 g of microbial cell powder of *Bifidobacterium bifidum*, and 100 g of microbial cell powder of lactobacilli/Bifidobacteria, which are triturated with starch, are added to prepare about 95 kg of modified milk powder blended with *Bifidobacterium bifidum*/human milk oligosaccharides (available from Funakoshi). When the obtained modified milk powder is dissolved in water, and becomes a milk preparation at a total solid content concentration of 14% (w/V) (as a standard milk preparation concentration), the number of bacteria of *Bifidobacterium bifidum* in the milk preparation may become $2.7 \times 10^9$ CFU/100 ml. When the modified milk powder obtained as described above is administered, proliferation of probiotics may be promoted in the intestine.

When the nutritional compositions produced in the above described Production Examples 1 to 5 are administered, probiotics can use HMOs and proliferate in the intestine, which leads to improvement of intestinal flora.

The invention claimed is:

1. A nutritional composition comprising:
   bacteria belonging to *Bifidobacterium bifidum*;
   one or more types of probiotics having a low ability to assimilate human milk oligosaccharides; and
   human milk oligosaccharides;
   wherein the probiotics are a bacterium strain selected from the group consisting of *Bifidobacterium longum* subspecies *longum* ATCC15707, *Bifidobacterium longum* subspecies *longum* BB536, *Bifidobacterium adolescentis* ATCC15703, *Bifidobacterium pseudocatenulatum* ATCC27919, *Bifidobacterium animalis* subspecies *lactis* DSM10140, *Bifidobacterium animalis* subspecies *lactis* MCC-525, *Bifidobacterium breve* ATCC15700, *Bifidobacterium pseudolongum* ATCC25526, *Bifidobacterium longum* (FERM P-10657), *Bifidobacterium animalis* subspecies *lactis* Bb-12 DSM1595, *Bifidobacterium animalis* subspecies *lactis* GCL2505, *Bifidobacterium animalis* subspecies *lactis* CNCMI-2494, *Bifidobacterium animalis* subspecies *lactis* LAFTI B94, *Bifidobacterium animalis* subspecies *lactis*, *Bifidobacterium longum* Rosell-175, *Bifidobacterium animalis* subspecies *animalis*, *Bifidobacterium animalis* subspecies *lactis* HN019, *Lactobacillus paracasei* ATCC25302, *Lactobacillus plantarum* ATCC14917, *Lactobacillus acidophilus* ATCC4356, *Lactobacillus rhamnosus* ATCC7469, *Lactobacillus gasseri* ATCC33323, *Lactobacillus gasseri* FERM BP-10953, *Lactobacilluss gasseri* FERM BP-6999, *Lactobacilluss gasseri*, (NITE BP-224R), *Lactobacillus delbrueckii* subspecies *bulgaricus* (FERM P-17227), *Lactobacillus rhamnosus* ATCC53103, *Lactobacillus reuteri* DSM17938, *Bacillus coagulans* GBI-30, *Lactobacillus acidophilus*, *Lactobacillus acidophilus* LAFTI L10, *Lactobacillus casei* LAFTI L26, *Lactococcus lactis* subspecies *lactis* Rosell-1058, *Lactobacillus paracasei* NCC2461, *Lactobacillus johnsonii* NCC533, *Lactobacillus rhamnosus* Rosell-11, *Lactobacillus acidophilus* Rosell-52, *Lactobacillus casei*, *Lactobacillus casei* shirota, and combinations thereof.

2. The nutritional composition according to claim 1, wherein the human milk oligosaccharides are 2'-fucosyllactose and/or lacto-N-neotetraose.

3. The nutritional composition according to claim 1, wherein the bacteria belonging to *Bifidobacterium bifidum* are a bacterium selected from the group consisting of *Bifidobacterium bifidum* ATCC29521, *Bifidobacterium bifidum* (NITE BP-2429), *Bifidobacterium bifidum* (NITE BP-1252), *Bifidobacterium bifidum* (NITE BP-2431), *Bifidobacterium bifidum* (NITE BP-02648), *Bifidobacterium bifidum* (NITE BP-02432), *Bifidobacterium bifidum* (NITE BP-02433), and combinations thereof.

4. A food/drink composition comprising the nutritional composition described in claim 1.

5. A modified milk powder comprising the nutritional composition described in claim 1.

6. A method for promoting proliferation of probiotics having a low ability to assimilate human milk oligosaccharides in the presence of human milk oligosaccharides, the method comprising co-culturing the probiotics with *Bifidobacterium bifidum* and human milk oligosaccharides,
wherein the probiotics are a bacterium strain selected from the group consisting of *Bifidobacterium longum* subspecies *longum* ATCC15707, *Bifidobacterium longum* subspecies *longum* BB536, *Bifidobacterium adolescentis* ATCC15703, *Bifidobacterium pseudocatenulatum* ATCC27919, *Bifidobacterium animalis* subspecies *lactis* DSM10140, *Bifidobacterium animalis* subspecies *lactis* MCC-525, *Bifidobacterium pseudolongum* ATCC25526, *Bifidobacterium longum* (FERM P-10657), *Bifidobacterium animalis* subspecies *lactis* Bb-12 DSM1595, *Bifidobacterium animalis* subspecies *lactis* GCL2505, *Bifidobacterium animalis* subspecies *lactis* CNCMI-2494, *Bifidobacterium animalis* subspecies *lactis* LAFTI B94, *Bifidobacterium animalis* subspecies *lactis*, *Bifidobacterium longum* Rosell-175, *Bifidobacterium animalis* subspecies *animalis*, *Bifidobacterium animalis* subspecies *lactis* HN019, *Lactobacillus paracasei* ATCC25302, *Lactobacillus plantarum* ATCC14917, *Lactobacillus acidophilus* ATCC4356, *Lactobacillus rhamnosus* ATCC7469, *Lactobacillus gasseri* ATCC33323, *Lactobacillus gasseri* FERM BP-10953, *Lactobacilluss gasseri* FERM BP-6999, *Lactobacilluss gasseri*, (NITE BP-224R), *Lactobacillus delbrueckii* subspecies *bulgaricus* (FERM P-17227), *Lactobacillus rhamnosus* ATCC53103, *Lactobacillus reuteri* DSM17938, *Bacillus coagulans* GBI-30, *Lactobacillus acidophilus*, *Lactobacillus acidophilus* LAFTI L10, *Lactobacillus casei* LAFTI L26, *Lactococcus lactis* subspecies *lactis* Rosell-1058, *Lactobacillus paracasei* NCC2461, *Lactobacillus johnsonii* NCC533, *Lactobacillus rhamnosus* Rosell-11, *Lactobacillus acidophilus* Rosell-52, *Lactobacillus casei*, *Lactobacillus casei shirota*, and combinations thereof.

7. The method according to claim 6, wherein the human milk oligosaccharides are 2'-fucosyllactose and/or lacto-N-neotetraose.

8. The method according to claim 6, wherein the bacteria belonging to *Bifidobacterium bifidum* are a bacterium strain selected from the group consisting of *Bifidobacterium bifidum* ATCC29521, *Bifidobacterium bifidum* (NITE BP-2429), *Bifidobacterium bifidum* (NITE BP-1252), *Bifidobacterium bifidum* (NITE BP-2431), *Bifidobacterium bifidum* (NITE BP-02648), *Bifidobacterium bifidum* (NITE BP-02432), *Bifidobacterium bifidum* (NITE BP-02433), and combinations thereof.

9. A method for promoting proliferation of probiotics having a low ability to assimilate human milk oligosaccharides in an intestine, the method comprising
administrating the nutritional composition according to claim 1,
wherein the probiotics have a low ability to assimilate human milk oligosaccharides in the nutritional composition.

* * * * *